United States Patent
Takaoka et al.

(10) Patent No.: US 6,258,382 B1
(45) Date of Patent: Jul. 10, 2001

(54) DRUG SUSTAINED-RELEASED BIOMATERIAL

(75) Inventors: Kunio Takaoka, 480-3, Minamiasama, Matsumoto-shi, Nagano-ken; Naoto Saito, Matsumoto; Takao Okada, Kakogawa, all of (JP)

(73) Assignees: Takai Chemical Co., Hyogen; Kunio Takaoka, Nagano, both of (JP)

( * ) Notice: Subject to any disclaimer, the term of this patent is extended or adjusted under 35 U.S.C. 154(b) by 0 days.

(21) Appl. No.: 09/480,050

(22) Filed: Jan. 10, 2000

(30) Foreign Application Priority Data

Feb. 24, 1999 (JP) .................................................. 11-045779

(51) Int. Cl.$^7$ .......................... A61K 38/17; A61K 47/34; C08G 63/06; C08G 63/08
(52) U.S. Cl. ............................. 424/486; 424/426; 514/2; 514/21; 524/17; 524/21; 525/450; 528/354
(58) Field of Search ..................................... 424/424, 425, 424/426, 486, 499, 501; 514/2, 8, 12, 21; 524/17, 21, 599; 525/450; 528/354

(56) References Cited

U.S. PATENT DOCUMENTS

| | | | |
|---|---|---|---|
| 4,942,035 | | 7/1990 | Churchill et al. .................... 424/423 |
| 5,019,094 | * | 5/1991 | Bezwada et al. .................... 606/230 |
| 5,360,892 | * | 11/1994 | Bonsignore et al. ................ 528/354 |
| 5,807,566 | * | 9/1998 | De Vlieger et al. ................. 424/409 |
| 6,083,524 | * | 7/2000 | Sawhney et al. .................... 424/426 |
| 6,177,094 | * | 1/2001 | Jiang ................................... 424/426 |
| 6,177,095 | * | 1/2001 | Sawhey et al. ...................... 424/426 |

FOREIGN PATENT DOCUMENTS

| | | |
|---|---|---|
| 2203861A | 8/1990 | (JP) . |
| 3045265A | 2/1991 | (JP) . |

OTHER PUBLICATIONS

Abstract of U.S. Patent No. 4,942,035, Derwent Info Ltd., 2000.

\* cited by examiner

Primary Examiner—Jeffrey E. Russel
(74) Attorney, Agent, or Firm—Kolisch Hartwell Dickinson McCormack & Heuser

(57) ABSTRACT

The present invention offers biomaterials exhibiting excellent sustained-release property and degradation property such as that polypeptides or the like having a biological activity can be continuously released for a prescribed life span in vivo. The said biomaterials consist of a copolymer prepared by the reaction of lactic acid and/or glycolic acid and p-dioxanone with polyethylene glycol as main components.

12 Claims, No Drawings

DRUG SUSTAINED-RELEASED BIOMATERIAL

TECHNICAL FIELD OF THE INVENTION

The present invention relates to biomaterials and, more particularly, it relates to biomaterials using a copolymer composition having an excellent biodegradation as a base and exhibiting excellent sustained-releasing and degradation properties such as that polypeptides or the like having a biological activity can be continuously released for a prescribed life span in vivo.

PRIOR ART

Polypeptides which are the hormones being present in small amount in Living body and acting therein have been known already and, since such polypeptides are now able to be produced in large quantities as a result of the progress of incubating technique in recently years instead of isolation of small amount by extraction or the like from living body, they now occupy an important position in various fields of application to living body.

However, stability of polypeptides in vivo is low and, therefore, their dose and frequency of administration become large for achieving the effect whereby occurrence of side effect and physical and mental burdens in the patients are becoming big. Under such a background, there has been a demand for functional materials which release the drug in a proper amount within a programmed period of time whereby many investigations have been carried out.

For example, aliphatic polyesters having hydroxycarboxylic acid such as polylactic acid, copolymer of lactic acid with glycolic acid, polyhydroxybutyric acid and poly(ε-caprolactone) showing a biodegradability in vivo as a basic structure and also polymers such as a copolymer by a combination of the above with p-dioxanone or trimethylene carbonate have been known.

However, affinity of those hydrophobic polymers with a polypeptide having a relatively high hydrophilicity is little and there is a problem that the initial elution of the polypeptide from the surface of the polymer matrix is big. In addition, there is a rate-determining relation between elution of the polypeptide and water permeating into the polymer and the polypeptide is eluted independently of the polymer matrix whereby there is no proportional relation between the required released duration and the degradation time in vivo and such a polymer is not suitable as a sustained-released biomaterial. Even in the case of a low molecular weight polymer in such an extent as an oligomer, its disappearance by degradation takes more than one month and that results in an affection to surrounding tissues. Thus, a difficulty in its application produces another problem.

Moreover, in the aliphatic polyester, the terminal group is a carboxyl group and, therefore, in the case of a basic polypeptide, the terminal group is coordinated with the polypeptide by means of ionic bond, etc. whereby there is still another problem that the polypeptide is not released within an expected period.

In place of such a hydrophobic polymer, the use of collagen, gelatin, albumin, fibrin, hyaluronic acid, alginic acid, etc. having a hydrophilicity has been investigated as well. However, since those materials are natural ones, their component, molecular weight, water retentivity, etc. are not constant. There is another problem in view of immunology that, during the purifying process, the substances having antigenicity cannot be removed completely. Still another problem is that a releasing time of the polypeptide from the polymer matrix is short.

Accordingly, for solving the above-mentioned problems, copolymers exhibiting both hydrophobic and hydrophilic properties of a lactic acid/glycolic acid copolymer or polylactic acid with polyethylene glycol, polypropylene glycol and Pluronic as the materials containing no impurities in the base, having no side effect and showing little affection to the surrounding cells have now been receiving public attention and various investigations have been carried out for them.

As an example for such an art, the Japanese Laid-Open Patent Publication Sho-58/191714 discloses a method where graft block polymer having a minimum average molecular weight of 5,000 which is able to form hydrogel by absorption of water under a circumstance of in water or in vivo is used as a pharmaceutical and veterinary composition. In this art, it is mentioned that a polymer obtained by polymerization of polyethylene glycol of molecular weight of 6,000 or 20,0000 and D,L-lactide or glycolide becomes gel by absorption of water within from 4 to 24 hours. However, for the polymer having such a big hydrophilic segment, the polymer swells and its shape gets to be crumbled and, therefore, adjustment between release of the drug and degradation of the polymer is difficult.

As a prior art, the present inventors have disclosed in the Japanese Laid-Open Patent Publication Hei-02/203861 for a biomaterial in which a reaction product of polylactic acid or a lactic acid/glycolic acid copolymer with polyethylene glycol as a carrier for a bone morphogenetic protein. However, although this material is a polymer which has both hydrophilic and hydrophobic properties being dispersed in water at low temperature while, when heated, being separated therefrom, there is still a problem that the said material is difficult in handling because it is in a pasty or waxy form. In another Japanese Laid-Open Patent Publication Hei-03/45265, the present inventors improved the adhesive property of the materials by blending (1) a lactic acid/glycolic acid copolymer and (2) a reaction product of a lactic acid/glycolic acid copolymer with polyethylene glycol. However, properties inherent to the two polymers strongly appear in terms of release of the drug and degradation of the polymer whereby a satisfactory result has not been achieved yet.

Further, Ronnenberger, B., et al. disclosed the use of a triblock copolymer of a lactic acid/glycolic acid copolymer with polyethylene glycol having a molecular weight of 1,000–10,000 as a biomaterial (*J. Biomed. Mater. Res.*, 30, 31 (1996)). This polymer ismade into a filmbymethylene chloride, its handling is good, and its molecular weight distribution obtained by dividing the weight average molecular weight by the number average molecular weight is 1.80–2.86. However, in a polymer where the molecular weight distribution is as broad as more than 1.8, the influence by aliphatic polyesters is appeared strongly and, therefore, the polymer is not suitable as a sustained-released biomaterial because of a poor balance between release of the drug and degradation of the polymer.

As mentioned above, many studies have been carried out up to now for the method where the drug such as polypeptide is contained. in a biomaterial and many proposals based upon them have been available but, at present, any biomaterial which is satisfactory in terms of releasing rate of the drug and also in terms of degradability, safety and practical value of the material has not been found yet.

Problems to be Solved by the Invention

In order to solve the above-mentioned problems, the present inventors have carried out an intensive investigation for developing biomaterials which are biodegradable, have both hydrophobic and hydrophilic properties, particularly exhibit excellent property for giving sustained release of polypeptide having a biological activity, show no xenobiotic reaction in vivo and have no affection to the surrounding tissues.

Means for Solving the Problems

As a result, the present inventors have found that a copolymer which is obtained by the reaction of lactic acid and/or glycolic acid and p-dioxanone with polyethylene glycol as main components can be used as excellent biomaterials for solving the above-mentioned problems when it (the copoleymer)is used carrying polypeptide or the like. Based upon such a finding, the present invention has been accomplished.

Thus, the present invention relates to biomaterials which consist of a copolymer obtained by the reaction of lactic acid and/or glycolic acid and p-dioxanone with polyethylene glycol as main components.

BEST MODE FOR CARRYING OUT THE INVENTION

The biomaterials according to the present invention use a copolymer which is obtained by the reaction of lactic acid and/or glycolic acid and p-dioxanone with polyethylene glycol as main components. Such a copolymer can be easily manufactured by the reaction of D,L-lactide and p-dioxanone with polyethylene glycol having one or more hydroxyl group(s) in the presence of a catalyst. The resulting copolymer is a block copolymer consisting of lactic acid, dioxanone and ethylene oxide units.

As to the polyethylene glycol used in this case, that having a number average molecular weight of within a range of about 600–20,000 is used. When the molecular weight is less than 600, the resulting copolymer has a fluidity when manufactured in a region where the ethylene oxide unit content is high while, when manufactured in a region where the said ethylene oxide unit content is low, biomaterials having a desired releasing rate are not obtained. On the other hand, when the molecular weight is more than 20,000, a bad affection to living body is resulted and that is not preferred.

Examples of the catalyst which is used in the reaction are stannous 2-ethylhaxanoate, dibutyltin dilaurate, stannous chloride, stannic chloride, diethylzinc, basic zinc carbonate, titanium tetraisopropoxide, tributyltin methoxide, dibutyltin oxide and aluminum isopropoxide.

Another mode of copolymerization reaction is that, after a lactide is firstly copolymerized with p-dioxanone by a ring-opening polymerization or, after a copolymer is manufactured by a direct dehydrating polycondensation of lactic acid with p-dioxanone, polyethylene glycol and a catalyst for esterification are added thereto to be able to conduct the reaction. In that case, phosphoric acid, benzenesulfonic acid, acid-type ion-exchange resin, etc. may be used as a catalyst for the esterification. In the case of a ring-opening polymerization, although the materials may be polymerized in a melted state, it is also possible to conduct the polymerization in a solvent which is capable of solubilizing the monomer or the polymer. The lactic acid used therefor may be any of D-, L- and DL-substances or a mixture thereof.

It is necessary that the total amount of lactic acid and/or glycolic acid, p-dioxanone and polyethylene glycol is 80% by weight or more and, if it is within such a range, other components/materials may be added to the copolymer. For example, in the manufacture of the copolymer, the reaction may be carried out by adding other hydroxycarboxylic acid such as trimethylene carbonate, polyfunctional polyol such as ethylene glycol, glycerol, sucrose and polypropylene glycol etc. to the materials although their amount is to be less than 20% by weight of the total amount of the copolymer.

It is also necessary that the ratio of the lactic acid and/or glycolic acid (A), p-dioxanone (B) and polyethylene glycol (C) in the copolymer in terms of a molar ratio of A:B:C is within a range of 26~60:4~25:25~70. When the molar ratio of polyethylene glycol (C) to lactic acid and/or glycolic acid (A) and p-dioxanone (B) is less than 25, the degradation rate of the resulting copolymer is significantly low even if the ratio of lactic acid and/or glycolic acid (A) to p-dioxanone (B) is changed to any extent. On the other hand, when the said molar ratio is more than 70, the resulting copolymer exhibits a strongly water-soluble property and is not suitable for an object of the biomaterials. In addition, the molar ratio of lactic acid and/or glycolic acid (A) to p-dioxanone (B) is within a range of 26~60:4~25 and, when the ratio is out of that range, degradation rate of the biomaterials becomes low and, furthermore, brittle hydrogel is formed whereby the product is not suitable as biomaterials.

The copolymer which is prepared by copolymerization is subjected to a treatment such as purification and, in the purifying treatment, a method where the copolymer is dissolved in acetone, chloroform, etc. and then 6- to 10-fold by volume of ether, petroleum ether, etc. are added to the amount of the copolymer whereby the copolymer is precipitated, a method where the copolymer is dispersed in 10-fold by volume of water at around 5° C. and the dispersion is heated whereby the copolymer is separated, etc. may be adopted. As a result of such a purifying treatment, polymers and homopolymers of low molecular weight which are impurities in the copolymer can be removed and, in addition, unreacted polyethylene glycol can be removed since the polyethylene glycol is soluble in the above-mentioned solvent or in an aqueous layer used for the purification.

The number average molecular weight of the copolymer prepared as such is within a range of from 2,300 to 47,000 and the molecular weight distribution obtained by dividing the weight average molecular weight by the number average molecular weight is within a range of from 1.04 to 1.50. The copolymer has both hydrophobic and hydrophilic properties as biomaterials and, especially when a biologically active substance such as polypeptide is contained therein, a stable release in vivo can be maintained.

The polypeptide which is a biologically active substance as such may be used in any of the cases where it is soluble in water and is hardly soluble therein. Examples of the types of the polypeptide are nerve growth factor, epidermal growth factor, fibroblast-derived growth factor, platelet-derived growth factor, colony stimulating factor, erythropoietin, interleukin-1, -2 and -3, interferon-α, -β and -γ, cartilage-derived factor, cartilage-derived growth factor, bone-derived growth factor, bone morphogenetic protein, pelvis growth factor, transforming growth factor, insulin and prostaglandin. Other examples are luteinizing hormone releasing hormone antagonist, somatostatin and derivatives thereof, growth hormone, prolactin, adrenocorticotropic hormone, melanocyte stimulating hormone, thyrotropin releasing hormone and salts and derivatives thereof, thyroid stimulating hormone, luteinizing hormone, follicle stimulating hormone, vasopressin and derivatives thereof, oxytocin, calcitonin, parathyroid hormone, glucagon, gastrin, secretin, cholecystokinin, angiotensin, human placental lactogen, human chorionic gonadotropin, enkephalin and derivatives thereof, endorphin, kyotorphin, tuftsin, thymopoietin II, thymosin, thymostimulin, thymic humoral factor, serum thymic factor and derivatives thereof as well as other thymic factors, tumor necrosis factor, colony stimulating factor, motilin, neurotensin, caerulein, urokinase, asparaginase, kallikrein, substance P, blood coagulation factors VIII and IX, lysozyme chloride, polymyxin B, colistin, gramicidin and bacitracin. It is further possible that the copolymer is used together with anti-inflammatory agents, antibiotics, antitumor agents, immunosuppressive agents, etc. and impregnated in or mixed with porous hydroxyapatite, Bio-Glas, ceravital, tricalcium phosphate, tetracalcium phosphate, calcium aluminate, etc. whereby the complexing effect is achieved.

Among the polypeptides listed hereinabove, the polypeptide which is most suitable for the biomaterials according to the present invention is bone morphogenetic protein. This bone morphogenetic protein is usually called BMP and is a substance which extracellularly acts the immature mesenchymal type cells and differentiates the genotype into chondrocytes and osteoblasts whereby cartilage and bone are induced. At present, BMP 1 to 13 have been confirmed. The BMP which is used in the present invention may be any of the substances prepared by means of a genetic recombination method and by means of isolation and purification from Dunn osteosarcoma (Takaoka, K., *Biomedical Research*, 2 (5), 466–471 (1981)) and there is no particular limitation for the method of manufacturing the same.

Method of preparation of the biomaterials according to the present invention may be carried out by common means for including the drug to include into a copolymer. For example, a copolymer is at first dissolved or dispersed in a solvent which is easily evaporated, then a polypeptide is homogeneously dispersed therein and the solvent used is removed therefrom. With regard to the solvent used therefor, acetone, methylene chloride, chloroform, ethanol, etc. are preferred and, depending upon the object of use of the biomaterials, one of those solvents may be used solely or two or more of them may be used jointly. Another method is that a copolymer is added to an aqueous solution of a polypeptide and, after the polypeptide is adsorbed as a result of swelling of the copolymer, it is freeze-drying. Still another method is that an emulsion of a copolymer mixed with a polypeptide and water is prepared and the solvent is removed from the emulsion to prepare microcapsules. It is also possible to prepare by means of mixing a polypeptide with a copolymer which is fluidized by warming. It is further possible that a copolymer of a low molecular weight is used to result in a fluidity, then a polypeptide is mixed therewith and the product in a state of keeping the fluid property is used. In addition, a copolymer used in the present invention may be sterilized by the use of autoclave, γ radiation, ethylene oxide gas, etc. if and when necessary.

EXAMPLES

The present invention will now be further illustrated by way of the following examples although the present invention is not limited thereto. Incidentally, % stands for that by weight in all cases unless otherwise mentioned.

Example 1

To a 50-ml reaction vessel were added 20 g of DL-lactide, 9.3 g of p-dioxanone and 10.4 g of polyethylene glycol with a number average molecular weight of 4000 (a reagent manufactured by Kishida Kagaku KK), then 52 µl of a 8% solution of stannous octanoate in diethyl ether were added thereto and the mixture was frozen at −48° C. After freezing, it was made evacuated in vacuo at 1 mmHg for one hour, sealed, made to react at 145° C. for 7 hours and further made to react at 160° C. for 9 hours.

The reaction product was dissolved in 100 ml of acetone with warming and 550 ml of diethyl ether was added to give a translucent precipitate. This was cooled at −45° C. for 30 minutes and the separated polymer was dried in vacuo at 70° C.

After drying in vacuo, 35 g of a copolymer were obtained. The copolymer was subjected to a measurement of molecular weight by means of a gel permeation chromatography (GPC) whereupon the number average molecular weight was 9,900, the weight average molecular weight was 11,900 and the molecular weight distribution was 1.2. When molar ratio of lactic acid, dioxanone and polyethylene glycol was determined by means of $^1$H-NMR, it was found to be 43:13:44. The glass transition temperature as measured by differential scanning calorimeter (DSC) was −7.9° C.

The resulting copolymer (50 mg) was dissolved in 500 µl of acetone with cooling and mixed with 10 µg of rhBMP-2 obtained by a genetic recombination and the mixture was dried in vacuo at 25° C. for 8 hours to prepare biomaterials of the present invention in a form of pellets. Then the biomaterials were implanted under the fasciae of the dorsal muscle in mice (5 weeks age). After three weeks, the implants were excised, their soft X-ray photograph and histological image were observed and calcium content was determined to check the state of bone tissues whereupon fibrous trabeculae were noted and bone formation was confirmed.

Comparative Example 1

In place of p-dioxanone which was a material for the manufacture of the copolymer used in Example 1, DL-lactide was used and a reaction was carried out in the presence of polyethylene glycol for the composition rate where the amount of the lactide increased. Then reaction and purification were carried out in the same manner as well to give 37 g of a copolymer. When its molecular weight was measured by GPC, the number average molecular weight was 8,700, the weight average molecular weight was 10,600 and the molecular weight distribution was 1.2. When molar ratio of lactic acid to polyethylene glycol was measured by $^1$H-NMR, it was found to be 57:43. The glasstransition temperature as measured by DSC was 10° C.

The resulting copolymer was mixed with 10 µg of rhBMP-2 in the same manner as in Example 1 and implanted under the fasciae of the dorsal muscle in mice (5 weeks age). After three weeks, the implants were excised, their soft X-ray photograph and histological image were observed and calcium content was determined to check the state of bone tissues whereupon bone formation was noted around the implants only and the copolymer material remained at the center. The same test was carried out using a BMP only without the use of the above material whereupon bone formation was not observed at all.

Example 2

The same reaction as in Example 1 was carried out using 29.4 g of L-lactide, 15.9 g of glycolide, 17.5 g of p-dioxanone and 24.6 g of polyethylene glycol with a number average molecular weight of 4,000 (a reagent manufactured by Kishida Kagaku KK) and a purification was carried out by the same manner as well to give 65.6 g of a copolymer. When the molecular weight of this copolymer was measured by GPC, the number average molecular weight was 9,100, the weight average molecular weight was 10,000 and the molecular weight distribution was 1.1. The molar ratio of lactic acid, glycolic acid, dioxanone and ethylene oxide units was measured by $^1$H-NMR and was found to be 24:19:8:49. Result of the measurement of glass transition temperature as measured by DSC was −10° C.

The copolymer (150 mg) was dissolved in 2 ml of acetone with cooling and mixed with 60 μg of rhBMP-2 obtained by means of a genetic recombination and the mixture was dried in vacuo at room temperature for 24 hours to give the biomaterials of the present invention in a form of pellets. The resulting biomaterials were implanted under the fasciae of the dorsal muscle in mice (5 weeks age). After three weeks, the implants were excised and soft X-ray photograph and histological image were observed and content of calcium was measured to check the state of the bone tissues whereupon the bone formation as same as in Example 1 was confirmed.

Example 3

The same reaction as in Example 1 was carried out using 14.4 g of DL-lactide, 5.1 g of p-dixoanone and 16.5 g of polyethylene glycol with a number average molecular weight of 4,000 to give 26 g of a copolymer. When the molecular weight of this copolymer was measured by GPC, the number average molecular weight was 8,000, the weight average molecular weight was 8,600 and the molecular weight distribution was 1.1. The molar ratio of lactic acid, dioxanone and ethylene oxide units was measured by $^1$H-NMR and was found to be 28:6:66. Result of the measurement of glass transition temperature as measured by DSC was −6° C. while melting point was 34° C. The copolymer (50 mg) was mixed with 25 μg of rhBMP-2, made into pellets and implanted under the fasciae of the dorsal muscle in mice by the same manner as in Example 1. After three weeks, state of bone formation was examined whereupon a good bone formation was confirmed.

Example 4

The same reaction as in Example 1 was carried out using 26 g of DL-lactide, 7.4 g of p-dioxanone and 7.5 g of polyethylene glycol with a number average molecular weight of 1,000 to give 32 g of a copolymer. When the molecular weight of this copolymer was measured by GPC, the number average molecular weight was 3,900, the weight average molecular weight was 4,300 and the molecular weight distribution was 1.1. The molar ratio of lactic acid, dioxanone and ethylene oxide units was measured by $^1$H-NMR and was found to be 59:11:30. Result of the measurement of glass transition temperature as measured by DSC was −9° C. Thecopolymer (50 mg) was mixed with 25 μg of rhBMP-2, made into pellets and implanted under the fasciae of the dorsal muscle in mice by the same manner as in Example 1. After three weeks, state of bone formation was examined whereupon a good bone formation was confirmed.

Example 5

The same reaction as in Example 1 was carried out using 25.7 g of L-lactide, 6.1 g of p-dioxanone, 11.3 g of polyethylene glycol with a number average molecular weight of 20000 and 8.5 g of trimethylene carbonate at 164° C. for 15 hours and a purification was carried out to give 29 g of a copolymer. When the molecular weight of this copolymer was measured by GPC, the number average molecular weight was 33,000, the weight average molecular weight was 45,000 and the molecular weight distribution was 1.4. The molar ratio of lactic acid, dioxanone, ethylene oxide and trimethylene carbonate units was measured by $^1$H-NMR and was found to be 39:5:47:9. Result of the measurement of melting point as measured by DSC was 41 C. rhBMP-2 (10 μg) was mixed with 100 μl of water, 50 mg of the above copolymer were added thereto and adsorbed therewith and a freeze-drying was carried out for 30 hours to give the biomaterials of the present invention in a form of pellets. The resulting biomaterials were implanted under the fasciae of the dorsal muscle in mice (5 weeks age). After three weeks, the implants were excised and soft X-ray photograph and histological image were observed and content of calcium was measured to check the state of the bone tissues whereupon the bone formation as same as in Example 1 was confirmed.

Example 6

To a 50-ml reaction vessel were added 28 g of DL-lactide, 4.5 g of p-dioxanone and 12.7 g of polyethylene glycol with a number average molecular weight of 4,000, then 52 μl of a 8% solution of stannous octanoate in diethyl ether were added thereto and the mixture was frozen at −48° C. After freezing, it was made evacuated in vacuo at 1 mmHg for one hour, sealed, made to react at 140° C. for 8 hours and further made to react at 155° C. for 11 hours. An operation where the reaction product was dispersed in one liter of water at 90° C. and a precipitate was collected therefrom was repeated for three times to conduct a purification. After a freeze-drying of the purified product, a copolymer was obtained in an amount of 34 g. When the copolymer was subjected to a measurement of molecular weight by GPC, the number average molecular weight was 9,600, the weight average molecular weight was 10,500 and the molecular weight distribution was 1.1. When molar ratio of lactic acid, dioxanone and ethylene oxide units was determined by means of $^1$H-NMR, it was found to be 45:4:51. The glass transition temperature as measured by DSC was −10.4° C. The resulting copolymer (10 mg) was added to 1 ml of an aqueous solution containing 100 μg of G-colony stimulating factor so that the G-colony stimulating factor was adsorbed therewith and then a freeze drying was conducted to give biomaterials of the present invention. The biomaterials (2 mg) were implanted in the dorsal subcutaneous pocket of the rat and numbers of leukocyte in the rat after 18 days were examined whereupon it was confirmed that leukocyte numbers of the rat were more than those in the case of a control where the biomaterials of the present invention were not used.

Merit of the Invention

The biomaterials of the present invention are homogeneously swollen when water is permeated therein and, therefore, a polypeptide which is contained therein is dissolved and diffusion of the solution is constant. Further, since the state of permeation of water is maintained, the biomaterials have a high affinity to living body and, unlike a hydrogel which becomes brittle in a hydrated state, they achieve elasticity and adhesive property at the temperature of living body and have a property that their shape is hardly crumbled by compression of the tissues of living body. The said property achieves an effect that the influence of the polypeptide contained in the biomaterials on a releasing rate is made small.

In addition, unlike other materials which remain even after elution of polypeptide, the copolymer constituting the biomaterials of the present invention is hydrolyzed in the living body and the molecular weight of the hydrophobic segments is apt to decrease whereby the copolymer has a property that, after elution of polypeptide, it quickly disappears. Accordingly, the biomaterials of the present invention are excellent in terms of adaptability in the use within a broad range.

What is claimed is:

1. Biomaterials comprising a copolymer prepared by the reaction of lactic acid and/or glycolic acid and p-dioxanone with polyethylene glycol as main components, wherein the ratio of lactic acid and/or glycolic acid (A), p-dioxanone (B) and polyethylene glycol (C) in terms of their molar ratio (A:B:C) is within a rane of 26~60:4~25:25~70.

2. The biomaterials according to claim 1, wherein the amount of lactic acid and/or glycolic acid and p-dioxanone and polyethylene glycol in the copolymer is 80% by weight or more.

3. The biomaterials according to claim 2, wherein polypeptide is contained in a copolymer which is obtained by the reaction of lactic acid and/or glycolic acid and p-dioxanone with polyethylene glycol as main components.

4. The biomaterials according to claim 3, wherein the polypeptide is a bone morphogenefic protein.

5. The biomaterials according to claim 2, wherein the number average molecular weight of the copolymer is with in a range of from 2,300 to 47,000 and the molecular weight distribution, which is a quotient of the weight average molecular weight divided by the number average molecular weight is within a range of from 1.04 to 1.50.

6. The biomaterials according to claim 5, wherein polypeptide is contained in a copolymer which is obtained by the reaction of lactic acid and/or glycolic acid and p-dioxahone with polyethylene glycol as main components.

7. The biomaterials according to claim 6, wherein the polyimide is a bone morphogenetic protein.

8. The biomaterials according to claim 1, wherein the number average molecular weight of the copolymer is within a range of from 2,300 to 47,000 and the molecular weight distribution, which is a quotient of the weight average molecular weight divided by the number average molecular weight is within a range of from 1.04 to 1.50.

9. The biomaterials according to claim 8, wherein polypeptide is contained in a copolymer which is obtained by the reaction of lactic acid and/or glycolic acid and p-dioxanone with polyethylene glycol as main components.

10. The biomaterials according to claim 9, wherein the polypeptide is a bone morphogenetic protein.

11. The biomaterials according to claim 1, wherein polypeptide is contained in a copolymer which is obtained by the reaction of lactic acid and/or glycolic acid and p-dioxanone with polyethylene glycol as main components.

12. The biomaterials according to claim 11, wherein the polypeptide is a bone morphogenetic protein.

* * * * *

UNITED STATES PATENT AND TRADEMARK OFFICE
CERTIFICATE OF CORRECTION

PATENT NO.    : 6,258,382 B1
DATED         : July 10, 2001
INVENTOR(S)   : Kunio Takaoka, Naoto Saito and Takao Okada It is certified that error appears in the above-identified patent and that said Letters Patent is hereby corrected as shown below:

Title page,
Item [73], Assignee, please delete "Takai Chemical Co., Hyogen; Kunio Takaoka, Nagano, both of (JP)" and insert -- Taki Chemical Co., Hyogen-ken; Kunio Takaoka, Nagano-ken, both of (JP) -- therefor --.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,258,382 B1 Page 1 of 1
DATED : July 10, 2001
INVENTOR(S) : Kunio Takaoka, Naoto Saito and Takao Okada It is certified that error appears in the above-identified patent and that said Letters Patent is hereby corrected as shown below:

<u>Title page,</u>
Item [73], should read:
-- [73]   Assignees:   Taki Chemical Co. Ltd., Hyogo-ken; Kunio Takaoka, Nagano-ken, both of (JP) --

Signed and Sealed this

Twenty-eighth Day of October, 2003

JAMES E. ROGAN
*Director of the United States Patent and Trademark Office*